(12) United States Patent
Judd et al.

(10) Patent No.: US 6,692,961 B1
(45) Date of Patent: Feb. 17, 2004

(54) DEFINED SYSTEMS FOR EPITHELIAL CELL CULTURE AND USE THEREOF

(75) Inventors: David A. Judd, Williamsville, NY (US); Paul J. Battista, Eggertsville, NY (US)

(73) Assignee: Invitrogen Corporation, Carlsbad, CA (US)

( * ) Notice: Subject to any disclaimer, the term of this patent is extended or adjusted under 35 U.S.C. 154(b) by 20 days.

(21) Appl. No.: 09/695,926

(22) Filed: Oct. 26, 2000

Related U.S. Application Data

(63) Continuation of application No. 08/948,053, filed on Oct. 9, 1997, now abandoned.
(60) Provisional application No. 60/028,471, filed on Oct. 11, 1996.

(51) Int. Cl.$^7$ ................................................. C12N 5/00

(52) U.S. Cl. ........................ 435/406; 435/404; 435/405

(58) Field of Search ................................ 435/325, 371, 435/404, 405, 406

(56) References Cited

U.S. PATENT DOCUMENTS

| | | | |
|---|---|---|---|
| 4,533,637 A | 8/1985 | Yamane et al. | 435/240 |
| 4,673,649 A | 6/1987 | Boyce et al. | 435/240 |
| 4,743,679 A | 5/1988 | Cohen et al. | 530/350 |
| 4,767,704 A | 8/1988 | Cleveland et al. | 435/68 |
| 4,940,666 A | 7/1990 | Boyce et al. | 435/240.2 |
| 5,122,469 A | 6/1992 | Mather et al. | 435/240.2 |
| 5,189,148 A | 2/1993 | Akiyama et al. | 530/399 |
| 5,292,655 A | 3/1994 | Wille, Jr. | 435/240.3 |
| 5,316,938 A | 5/1994 | Keen et al. | 435/240.31 |
| 5,342,777 A | 8/1994 | Cole et al. | 435/240.31 |
| 5,364,785 A | 11/1994 | Mather et al. | 435/240.2 |
| 5,378,612 A | 1/1995 | Nakashima et al. | 435/69.6 |
| 5,395,756 A | 3/1995 | Igarashi | 435/69.4 |
| 5,443,968 A | 8/1995 | Takazawa et al. | 435/70.3 |
| 5,461,030 A | 10/1995 | Lindenbaum | 544/4 |
| 5,474,931 A | 12/1995 | DiSorbo et al. | 435/240.31 |
| 5,573,957 A | 11/1996 | Cardone et al. | 436/518 |
| 5,576,194 A | 11/1996 | Chan | 435/69.6 |
| 5,631,159 A | 5/1997 | Marshall et al. | 435/383 |
| 5,633,162 A | 5/1997 | Keen et al. | 435/384 |
| 5,641,647 A | 6/1997 | Fischer et al. | 435/69.1 |
| 6,103,529 A | 8/2000 | Price et al. | 435/404 |

FOREIGN PATENT DOCUMENTS

| | | |
|---|---|---|
| EP | 0 408 146 A2 | 1/1991 |
| EP | 0 481 791 A2 | 4/1992 |
| EP | 0 531 733 A1 | 3/1993 |
| WO | WO 90/08771 | 8/1990 |
| WO | WO 92/05246 | 4/1992 |
| WO | WO 95/01434 | 1/1995 |
| WO | WO 97/34999 | 9/1997 |
| WO | WO 98/24883 | 6/1998 |

OTHER PUBLICATIONS

Boyce, S.T., and Ham, R.G., "Calcium–Regulated Differentiation of Normal Human Epidermal Keratinocytes in Chemically Defined Clonal Culture and Serum–Free Serial Culture," *J. Invest. Dermatol.* 81:33s–40s, The Williams and Wilkins Co. (1983).

Chaproniere–Rickenberg, D.M., and Webber, M.M., "Zinc Levels in Zinc–Stabilized Insulin are Inhibitory to the Growth of Cells In Vitro," In Vitro 19(5):373–375, Tissue Culture Association (1983).

Daley, J.P., et al., "Growth of Human Epidermal Keratinocytes in Keratinocyte Serum–Free Medium," *Focus* 12(3):68–71, Life Technologies, Inc. (1990).

Ethier, S.P., et al., "Influence of Hormone and Growth Factor Interactions on the Proliferative Potential of Normal Rat Mammary Epithelial Cells In Vitro," *J. Cell. Physiol.* 132:161–167, Alan R. Liss, Inc. (1987).

Gilchrest, B.A., et al., "Characterization and Partial Purification of Keratinocyte Growth Factor From the Hypothalamus," *J. Cell. Physiol.* 120:377–383, Alan R. Liss, Inc. (1984).

Gilchrest, B.A., et al., "Attachment and Growth of Human Keratinocytes in a Serum–Free Environment," *J. Cell. Physiol.* 112:197–206, Alan R. Liss, Inc. (1982).

Gill, D.M., "Mechanism of Action of Cholera Toxin," in *Advances in Cyclic Nucleotides Research*, vol. 8, P. Greengard and G.A. Robinson, eds., New York, Raven Press, pp. 85–118 (1977).

Gospodarowicz, D., and Cheng, J., "Heparin Protects Basic and Acidic FGF From Inactivation," *J. Cell. Physiol.* 128:475–484, Alan R. Liss, Inc. (1986).

Green, W.N., et al., "cAMP stimulation of acetylcholine receptor expression is mediated through posttranslational mechanisms," *Proc. Natl. Acad. Sci. USA* 88:854–858, National Academy of Sciences of the USA (1991).

Hahm, H.A., and Ip, M.M., "Primary Culture of Normal Rat Mammary Epithelial Cells Within a Basement Membrane Matrix. I. Regulation of Proliferation by Hormones and Growth Factors," *In Vitro Cell. Dev. Biol.* 26:791–802, Tissue Culture Association (1990).

(List continued on next page.)

Primary Examiner—Jean C. Witz
(74) Attorney, Agent, or Firm—Sterne, Kessler, Goldstein & Fox PLLC.

(57) ABSTRACT

The present invention provides cell culture media formulations which support the in vitro cultivation of animal epithelial cells. The media comprise at least one fibroblast growth factor (FGF) and at least one agent that induces increased intracellular cAMP levels, and optionally comprise ascorbic acid. The present invention also provides methods of cultivating animal epithelial cells in vitro using these cell culture media formulations, kits comprising the media, cell culture compositions comprising the culture media and an animal epithelial cell, and compositions that may be used as replacements for organ or gland extracts in animal cell culture media.

59 Claims, 6 Drawing Sheets

OTHER PUBLICATIONS

Hahm, H.A., et al., "Primary Culture of Normal Rat Mammary Epithelial Cells Within a Basement Membrane Matrix. II. Functional Differentiation Under Serum–Free Conditions," *In Vitro Cell. Dev. Biol.* 26:803–814, Tissue Culture Association (1990).

Ham, R.G., "Formulation of Basal Nutrient Media," in *Methods for Preparation of Media, Supplements, and Substrata for Serum–Free Animal Cell Culture*, Barnes, D.W., et al., eds., New York, Alan R. Liss, Inc., pp. 3–21 (1984).

Imagawa, W., et al., "Keratinocyte Growth Factor and Acidic Fibroblast Growth Factor Are Mitogens for Primary Cultures of Mammary Epithelium," *Biochem. Biophys. Res. Commun.* 204:1165–1169, Academic Press, Inc. (1994).

Lambert, K.J., and Birch, J.R., "Cell Growth Media," in *Animal Cell Biotechnology*, vol. 1, Spier, R.E., and Griffiths, J.B., eds., New York, Academic Press, Inc., pp. 85–122 (1985).

Marcelo, C.L., et al., "Stratification, Specialization, and Prolferation of Primary Keratinocyte Cultures," *J. Cell. Biol.* 79:356–370, The Rockefeller University Press (1978).

Pirisi, L., et al., "Transformation of Human Fibroblasts and Keratinocytes with Human Papillomavirus Type 16 DNA," *J. Virol.* 61:1061–1066, American Society for Microbiology (1987).

Pittelkow, M.R., and Scott, R.E., "New Techniques for the In Vitro Culture of Human Skin Keratinocytes and Perspectives on Their Use for Grafting of Patients With Extensive Burns," *Mayo Clin. Proc.* 61:771–777, Mayo Foundation for Medical Education and Research (1986).

Pittelkow, M.R., and Shipley, G.D., "Serum–Free Culture of Normal Human Melanocytes: Growth Kinetics and Grwoth Factor Requirements," *J. Cell Physiol.* 140:565–576, Alan R. Liss, Inc. (1989).

Price, F.M., et al., "A New Culture Medium for Human Skin Epithelial Cells," In Vitro 16:147–158, Tissue Culture Association (1980).

Rheinwald, J.G., and Green, H., "Serial Cultivation of Strains of Human Epidermal Keratinocytes: the Formation of Keratinzing Colonies from Single Cells," *Cell 6*:331–344, MIT Press (1975).

Shipley, G.D., and Pittelkow, M.R., "Control of Growth and Differentiation In Vitro of Human Keratinocytes Cultured in Serum–free Medium," *Arch. Dermatol.* 123:1541a–1544a, American Medical Association (1987).

Shipley, G.D., et al., "Growth of Normal Keratinocytes and Fibroblasts in Serum–Free Medium Is Stimulated by Acidic and Basic Fibroblast Growth Factor," *J. Cell. Physiol.* 138:511–518, Alan R. Liss, Inc. (1989).

Turner, T., et al., "Serum–Free Culture of Enriched Mouse Anterior and Ventral Prostatic Epithelial Cells in Collagen Gel," *In Vitro Cell. Dev. Biol.* 26:722–730, Tissue Culture Association (1990).

Watson, C.A., et al., "Variability Among Human Umbilical Vein Endothelial Cultures," *Science 268*:447–448, American Association for the Advancement of Science (Apr. 1995).

Waymouth, C., "Preparation and Use of Serum–Free Culture Media," in *Methods for Preparation of Media, Supplements, and Substrata for Serum–Free Animal Cell Culture*, Barnes, D.W., et al., eds., New York, Alan R. Liss, Inc., pp.23–68 (1984).

Wille, J.J., Jr., et al., "Integrated Control of Growth and Differentiation of Normal Human Prokeratinocytes Cultured in Serum–Free Medium: Clonal Analyses, Growth Kinetics, and Cell Cycle Studies," *J. Cell. Physiol.* 121:31–44, Alan R. Liss, Inc. (1984).

Willey, J.C., et al., "Relationship of Ornithine Decarboxylase Activity and cAMP Metabolism to Proliferation of Normal Human Bronchial Epithelial Cells," *J. Cell. Physiol.* 124:207–212, Alan R. Liss, Inc. (1985).

DEFINED SYSTEMS FOR EPITHELIAL CELL CULTURE AND USE THEREOF

CROSS REFERENCE TO RELATED APPLICATION

This application is a continuation of U.S. Application Ser. No. 08/948,053, filed Oct. 9, 1997 now abandoned, which claims priority to U.S. Provisional Patent Application No. 60/028,471, filed Oct. 11, 1996, the contents of which are incorporated herein by reference.

BACKGROUND OF THE INVENTION

1. Field of the Invention

The present invention relates generally to cell culture medium formulations. Specifically, the present invention provides systems comprising defined cell culture medium formulations that facilitate the in vitro cultivation of epithelial cells, particularly keratinocytes. The present invention also provides methods for cultivation of animal cells using these systems.

2. Related Art

Cell Culture Media

Cell culture media provide the nutrients necessary to maintain and grow cells in a controlled, artificial and in vitro environment. Characteristics and compositions of the cell culture media vary depending on the particular cellular requirements. Important parameters include osmolarity, pH, and nutrient formulations.

Media formulations have been used to cultivate a number of cell types including animal, plant and bacterial cells. Cells cultivated in culture media catabolize available nutrients and produce useful biological substances such as monoclonal antibodies, hormones, growth factors and the like. Such products have therapeutic applications and, with the advent of recombinant DNA technology, cells can be engineered to produce large quantities of these products. Thus, the ability to cultivate cells in vitro is not only important for the study of cell physiology, but is also necessary for the production of useful substances which may not otherwise be obtained by cost-effective means.

Cell culture media formulations have been well documented in the literature and a number of media are commercially available. In early cell culture work, media formulations were based upon the chemical composition and physicochemical properties (e.g., osmolality, pH, etc.) of blood and were referred to as "physiological solutions" (Ringer, S., *J. Physiol.*, 3:380–393 (1880); Waymouth, C., In: *Cells and Tissues in Culture*, Vol. 1, Academic Press, London, pp. 99–142 (1965);Waymouth, C., *In Vitro* 6:109–127 (1970)). However, cells in different tissues of the mammalian body are exposed to different microenvironments with respect to oxygen/carbon dioxide partial pressure and concentrations of nutrients, vitamins, and trace elements; accordingly, successful in vitro culture of different cell types will often require the use of different media formulations. Typical components of cell culture media include amino acids, organic and inorganic salts, vitamins, trace metals, sugars, lipids and nucleic acids, the types and amounts of which may vary depending upon the particular requirements of a given cell or tissue type.

Typically, cell culture media formulations are supplemented with a range of additives, including undefined components such as fetal bovine serum (FBS) (10–20% v/v) or extracts from animal embryos, organs or glands (0.5–10% v/v). While FBS is the most commonly applied supplement in animal cell culture media, other serum sources are also routinely used, including newborn calf, horse and human. Organs or glands that have been used to prepare extracts for the supplementation of culture media include submaxillary gland (Cohen, S., *J. Biol. Chem.* 237:1555–1565 (1961)), pituitary (Peehl, D. M., and Ham, R. G., *In Vitro* 16:516–525 (1980); U.S. Pat. No. 4,673,649), hypothalamus (Maciag, T., et al., *Proc. Natl. Acad. Sci. USA* 76:5674–5678 (1979); Gilchrest, B. A., et al., *J. Cell. Physiol.* 120:377–383 (1984)), ocular retina (Barretault, D., et al., *Differentiation* 18:29–42 (1981)) and brain (Maciag, T., et al., *Science* 211:1452–1454 (1981)). These types of chemically undefined supplements serve several useful functions in cell culture media (Lambert, K. J. et al., In: *Animal Cell Biotechnology*, Vol. 1, Spier, R. E. et al., Eds., Academic Press New York, pp. 85–122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum or organ/gland extracts are commonly used as relatively low-cost supplements to provide an optimal culture medium for the cultivation of animal cells.

Unfortunately, the use of serum or organ/gland extracts in tissue culture applications has several drawbacks (Lambert, K. J. et al., In: *Animal Cell Biotechnology*, Vol 1, Spier, R. E. et al., Eds., Academic Pres New York, pp. 85–122 (1985)). For example, the chemical composition of these supplements may vary between lots, even from a single manufacturer. The supplements may also be contaminated with infectious agents (e.g., mycoplasma and viruses) which can seriously undermine the health of the cultured cells when these contaminated supplements are used in cell culture media formulations. Cell surface chemistry, which is a critical portion of the in vitro microenvironment for many cell types, can be adversely modified via adsorption or incorporation of serum or extract proteins. The use of undefined components such as serum or animal extracts also prevents the true definition and elucidation of the nutritional and hormonal requirements of the cultured cells, thus eliminating the ability to study, in a controlled way, the effect of specific growth factors or nutrients on cell growth and differentiation in culture. Moreover, undefined supplements prevent the researcher from studying aberrant growth and differentiation and the disease-related changes in cultured cells. Finally and most importantly to those employing cell culture media in the industrial production of biological substances, serum and organ/gland extract supplementation of culture media can complicate and increase the costs of the purification of the desired substances from the culture media due to nonspecific co-purification of serum or extract proteins.

Defined Media

To overcome these drawbacks of the use of serum or organ/gland extracts, a number of so-called "defined" media have been developed. These media, which often are specifically formulated to support the culture of a single cell type, contain no undefined supplements and instead incorporate defined quantities of purified growth factors, proteins, lipoproteins and other substances usually provided by the serum or extract supplement. Since the components (and concentrations thereof) in such culture media are precisely known, these media are generally referred to as "defined culture media." Often used interchangeably with "defined culture media" is the term "serum-free media" or "SFM." A number of SFM formulations are commercially available, such as those designed to support the culture of endothelial cells, keratinocytes, monocytes/macrophages, fibroblasts, chondrocytes or hepatocytes which are available from GIBCO/LTI (Gaithersburg, Md.). The distinction between SFM and defined media, however, is that SFM are media devoid of serum, but not necessarily of other undefined components such as organ/gland extracts. Indeed, several SFM that have been reported or that are available commercially contain such undefined components, including several formulations supporting in vitro culture of keratinocytes (Boyce, S. T., and Ham, R. G., *J. Invest. Dermatol.* 81:33 (1983); Wille, J. J., et al., *J. Cell. Physiol.* 121:31 (1984); Pittelkow, M. R., and Scott, R. E., *Mayo Clin. Proc.* 61:771 (1986); Pirisi, L., et al., *J. Virol.* 61:1061 (1987); Shipley, G. D., and Pittelkow, M. R., *Arch. Dermatol.* 123:1541 (1987); Shipley, G. D., et al., *J. Cell. Physiol.* 138:511–518 (1989); Daley, J. P., et al., *FOCUS (GIBCO/LTI)* 12:68 (1990); U.S. Pat. Nos. 4,673, 649 and 4,940,666). SFM thus cannot be considered to be defined media in the true definition of the term.

Defined media generally provide several distinct advantages to the user. For example, the use of defined media facilitates the investigation of the effects of a specific growth factor or other medium component on cellular physiology, which may be masked when the cells are cultivated in serum- or extract-containing media. In addition, defined media typically contain much lower quantities of protein (indeed, defined media are often termed "low protein media") than those containing serum or extracts, rendering purification of biological substances produced by cells cultured in defined media far simpler and more cost-effective.

Some extremely simple defined media, which consist essentially of vitamins, amino acids, organic and inorganic salts and buffers have been used for cell culture. Such media (often called "basal media"), however, are usually seriously deficient in the nutritional content required by most animal cells. Accordingly, most defined media incorporate into the basal media additional components to make the media more nutritionally complex, but to maintain the serum-free and low protein content of the media. Examples of such components include serum albumin from bovine (BSA) or human (HSA); certain growth factors derived from natural (animal) or recombinant sources such as EGF or FGF; lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements (reviewed by Waymouth, C., in: *Cell Culture Methods for Molecular and Cell Biology, Vol. 1: Methods for Preparation of Media, Supplements, and Substrata for Serum-Free Animal Cell Culture*, Barnes, D. W., et al., eds., New York: Alan R. Liss, Inc., pp. 23–68 (1984), and by Gospodarowicz, D., *Id.*, at pp 69–86 (1984)).

Epithelial Cells

Overview

The epithelium lines the internal and external surfaces of the organs and glands of higher organisms. Because of this localization at the external interface between the environment and the organism (e.g., the skin) or at the internal interface between an organ and the interstitial space (e.g., the intestinal mucosal lining), the epithelium has a major role in the maintenance of homeostasis. The epithelium carries out this function, for example, by regulating transport and permeability of nutrients and wastes (Freshney, R. I., in: *Culture of Epithelial Cells*, Freshney, R. I., ed., New York: Wiley-Liss, pp. 1–23 (1992)).

The cells making up the epithelium are generically termed epithelial cells. These cells may be present in multiple layers as in the skin, or in a single layer as in the lung alveoli. As might be expected, the structure, function and physiology of epithelial cells are often tissue-specific. For example, the epidermal epithelial cells of the skin are organized as stratified squamous epithelium and are primarily involved in forming a protective barrier for the organism, while the secretory epithelial cells of many glands are often found in single layers of cuboidal cells that have a major role in producing secretory proteins and glycoproteins. Regardless of their location or function, however, epithelial cells are usually regenerative. That is, under normal conditions, or in response to injury or other activating stimulus, epithelial cells are capable of dividing or growing. This regenerative capacity has facilitated the in vitro manipulation of epithelial cells, to the point where a variety of primary epithelial cells and cell lines have been successfully cultivated in vitro (Freshney, *Id*).

Keratinocytes

The specialized epithelial cells found in the epidermis of the skin are known as keratinocytes. In the upper, cornified layers of the skin (those exposed to the environment), the cytoplasm of the keratinocytes is completely replaced with keratin and the cells are dead. The keratinocytes located in the lower layers, however, particularly in the basal epidermis (stratum basale), actively divide and ultimately migrate up through the more superficial layers to replace those cells being sloughed off at the external surface. Accordingly, the skin can be thought of as a dynamic organ comprising keratinocytes that are constantly dividing, maturing and ultimately dying.

Cultures of human keratinocytes are increasingly being used in examinations of skin structure and disease, and as in vitro models of human skin in toxicology studies (Boyce, S. T., and Ham, R. G., in: *In Vitro Models for Cancer Research*, vol. III, Webber, M. M., et al., eds., Boca Raton, Fla.: CRC Press, Inc., pp. 245–274 (1985)). Successful culture of keratinocytes has proven, however, to be somewhat difficult, owing primarily to their nutritional fastidiousness (Gilchrest, B. A., et al., *J. Cell. Physiol.* 120:377–383 (1984)). For example, in most early studies using traditional serum-supplemented culture media, keratinocytes from skin explants were rapidly overgrown by less fastidious and faster-growing fibroblasts that were also resident in the tissue (Freshney, *Id.*). Thus, there has been substantial work expended in the attempt to formulate culture media favoring the selection and successful in vitro cultivation of human keratinocytes.

Keratinocyte Culture Medium Formulations and Systems

A variety of systems have been developed to culture human keratinocytes. Early work in this area used specialized culture media such as Medium 199 (Marcelo, C. L., et al., *J. Cell Biol.* 79:356 (1978)) and NCTC 168 (Price, F. M., et al., In Vitro 16:147 (1980)) supplemented with serum. Alternatively, keratinocyte growth and colony formation have been shown to be improved by plating cells on lethally irradiated 3T3 fibroblasts and by adding epidermal growth factor (EGF) and hydrocortisone to the medium (Rheinwald, J. G., and Green, H., *Cell* 6:331 (1975)). One of the first serum-free medium formulations developed for keratinocyte culture was based on Medium 199 and included a growth factor cocktail comprising bovine brain extract (Gilchrest, B. A., et al., *J. Cell. Physiol.* 112:197 (1982)), and serum-free culture of human keratinocytes without the use of 3T3 fibroblast feeder layers became widely accepted upon the development of a more specialized basal medium, MCDB-153 (Boyce, S. T., and Ham, R. G., *J. Invest. Dermatol.* 81:33 (1983); U.S. Pat. Nos. 4,673,649 and 4,940,666). Serum-free MCDB-153 includes trace elements, ethanolamine, phosphoethanolamine, hydrocortisone, EGF, and bovine pituitary extract (BPE). This medium and several enhanced versions have been used widely for human keratinocyte cultivation (Pittelkow, M. R., and Scott, R. E., *Mayo Clin. Proc.* 61:771 (1986); Pirisi, L., et al., *J. Virol.* 61:1061 (1987); Shipley, G. D., and Pittelkow, M. R., *Arch. Dermatol.* 123:1541 (1987); Daley, J. P., et al., *FOCUS (GIBCO/LTI)* 12:68 (1990)). The use of BPE is also common to many commercially available media for keratinocyte cultivation, including KGM (Clonetics Corporation; San Diego, Calif.), CS-2.0 Keratinocyte Cell Growth Medium (Cell Systems, Inc.; Kirkland, Wash.), M154 (Cascade Biologicals, Inc.; Portland, Oreg.) and Keratinocyte-SFM (GIBCO/LTI; Gaithersburg, Md.).

Serum-free medium containing BPE as the primary mitogen, however, has several drawbacks, as generally described above. For example, the undefined composition of BPE complicates experimental models and interpretation of results, and may either stimulate or inhibit the growth or differentiation of keratinocyte cultures, depending on the concentrations of other components in the medium (Wille, J. J., et al., *J. Cell. Physiol.* 121:31 (1984)). In addition, BPE requires titration in different cell systems, and its stability in medium is limited to about four weeks under normal use and storage conditions. There has been at least one report of a fully defined medium for the culture of epidermal cells, wherein BPE is replaced with epidermal growth factor (EGF), insulin-like growth factor 1 (IGF-1) and increased quantities of six specific amino acids (U.S. Pat. No. 5,292,655). However, this medium was designed for the specific purpose of in vitro formation of a skin substitute comprising differentiated keratinocytes, and may not be ideal for supporting continuous cultures of actively growing cells.

Thus, a need remains for defined culture media, that are serum- and organ/gland extract-free, for the cultivation of animal epithelial cells including keratinocytes. Such culture media will facilitate studies of the effects of growth factors and other stimuli on cellular physiology, will allow easier and more cost-effective purification of biological substances produced by cultured animal cells in the biotechnology industry, and will provide more consistent results in methods employing the cultivation of animal epithelial cells. The current invention provides such defined media.

SUMMARY OF THE INVENTION

The present invention provides defined culture media that replace BPE with growth-promoting additives such as insulin, EGF and other additives. Specifically, the invention provides a cell culture medium, capable of supporting the cultivation of an animal epithelial cell in vitro, comprising insulin, EGF, and at least two additional additives from the group consisting of FGF, an agent that increases intracellular levels of cyclic adenosine monophosphate (cAMP) and ascorbic acid. The medium provided by the present invention may be a 1×formulation, or may be concentrated as a 10× or higher formulation. The basal medium of the present invention comprises a number of ingredients, including amino acids, vitamins, organic and inorganic salts, sugars and other components, each ingredient being present in an amount which supports the cultivation of an animal epithelial cell in vitro. The medium may be used to culture a variety of animal epithelial cells, including primary cells (e.g., keratinocytes or cervical epithelial cells) and established cell lines (e.g., HeLa cells). Cells supported by the medium of the present invention may be derived from any animal, preferably a mammal, and most preferably a human. The present invention also provides methods of culturing animal epithelial cells using the culture medium formulations disclosed herein, comprising the steps of (a) contacting an animal cell with the cell culture medium of the present invention; and (b) cultivating the animal cell under conditions suitable to support its cultivation in vitro. The invention also provides kits for use in the cultivation of an animal epithelial cell. Kits according to the present invention comprise a carrier means having in close confinement therein one or more container means, wherein a first container means contains a basal culture medium as described above, a second carrier means contains a insulin, a third container means contains EGF, a fourth container means contains FGF, a fifth container means contains at least one agent that increases intracellular levels of cAMP, a sixth container means contains heparin and a seventh container means contains ascorbic acid. In a preferred embodiment, the second container means of the kits contains insulin, EGF, FGF, at least one agent that increases intracellular levels of cAMP, heparin and ascorbic acid together in admixture. The invention further provides cell culture compositions comprising the culture media of the present invention and an animal epithelial cell. The invention also provides compositions comprising heparin, EGF, FGF, at least one agent that increases intracellular levels of cAMP, and optionally ascorbic acid, which compositions may be used to replace organ or gland extracts in serum-free animal cell culture media. The culture media of the present invention are suitable for use in the isolation and initiation of primary epithelial cell cultures, as well as for the expansion of established epithelial cell cultures. Additionally, the media of the present invention provide superior growth, and maintenance of morphological and physiological markers, of primary animal epithelial cells.

DETAILED DESCRIPTION OF THE INVENTION

Definitions

Figure 1A:
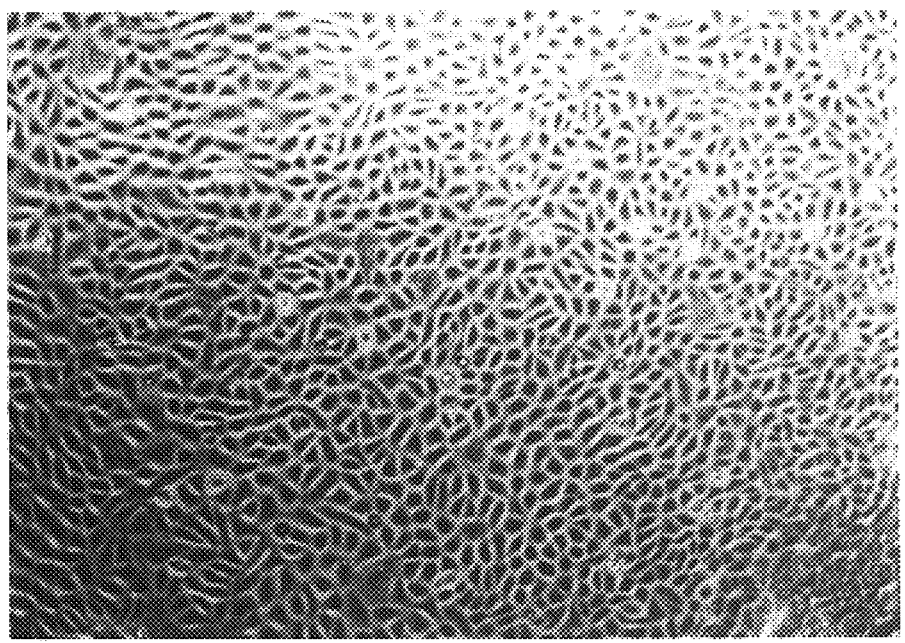
FIG. 1. Photomicrographs of phase contrast microscopy of human keratinocytes. Cells were cultured in the defined keratinocyte SFM of the present invention (panel A) or in a BPE-containing keratinocyte SFM (panel B). Photographs are 100×.

In the description that follows, a number of terms conventionally used in the field of cell culture media are utilized extensively. In order to provide a clear and consistent understanding of the specification and claims, and the scope to be given such terms, the following definitions are provided.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

By "cultivation" is meant the maintenance of cells in vitro under conditions favoring growth, differentiation or continued viability, in an active or quiescent state, of the cells. In this sense, "cultivation" may be used interchangeably with "cell culture" or any of its synonyms described above.

By "culture vessel" is meant a glass, plastic, or metal container that can provide an aseptic environment for culturing cells.

The phrases "cell culture medium," "culture medium" (plural "media" in each case) and "medium formulation" refer to a nutritive solution for cultivating cells and may be used interchangeably.

The term "contacting" refers to the placing of cells to be cultivated in vitro into a culture vessel with the medium in which the cells are to be cultivated. The term "contacting" encompasses mixing cells with medium, pipetting medium onto cells in a culture vessel, and submerging cells in culture medium.

The term "combining" refers to the mixing or admixing of ingredients in a cell culture medium formulation.

A cell culture medium is composed of a number of ingredients and these ingredients vary from one culture medium to another. A "1×formulation" is meant to refer to any aqueous solution that contains some or all ingredients found in a cell culture medium at working concentrations. The "1×formulation" can refer to, for example, the cell culture medium or to any subgroup of ingredients for that medium. The concentration of an ingredient in a 1×solution is about the same as the concentration of that ingredient found in a cell culture formulation used for maintaining or cultivating cells in vitro. A cell culture medium used for the in vitro cultivation of cells is a 1×formulation by definition. When a number of ingredients are present, each ingredient in a 1×formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic aced. A "1×formulation" of these amino acids contains about the same concentrations of these ingredients in solution. Thus, when referring to a "1×formulation," it is intended that each ingredient in solution has the same or about the same concentration as that found in the cell culture medium being described. The concentrations of ingredients in a 1×formulation of cell culture medium are well known to those of ordinary skill in the art. See *Methods For Preparation of Media, Supplements and Substrate For Serum-Free Animal Cell Culture* Allen R. Liss, N.Y. (1984), which is incorporated by reference herein in its entirety. The osmolarity and/or pH, however, may differ in a 1×formulation compared to the culture medium, particularly when fewer ingredients are contained in the 1×formulation.

A "10×formulation" is meant to refer to a solution wherein each ingredient in that solution is about 10 times more concentrated than the same ingredient in the cell culture medium. For example, a 10×formulation of RPMI-1640 culture medium may contain, among other ingredients, 2.0 g/L L-arginine, 0.5 g/L L-asparagine, and 0.2 g/L L-aspartic acid (compare 1×formulation, above). A "10× formulation" may contain a number of additional ingredients at a concentration about 10 times that found in the 1×culture medium. As will be readily apparent, "25×formulation," "50×formulation," "100×formulation," "500×formulation," and "1000×formulation" designate solutions that contain ingredients at about 25-, 50-, 100-, 500-, or 1000-fold concentrations, respectively, as compared to a 1×cell culture medium. Again, the osmolarity and pH of the media formulation and concentrated solution may vary.

Formulation of Culture Media
Basal Media

The cell culture media of the present invention are aqueous-based, comprising a number of ingredients in a solution of deionized, distilled water to form "basal media." Ingredients which the basal media of the present invention may include are amino acids, vitamins, inorganic salts, adenine, ethanolamine, D-glucose, heparin, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, triiodothyronine (T3), thymidine and transferrin. Alternatively, insulin and transferrin may be replaced by ferric citrate or ferrous sulfate chelates. Each of these ingredients may be obtained commercially, for example from Sigma (Saint Louis, Mo.).

Amino acid ingredients which may be included in the media of the present invention include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially, for example from Sigma (Saint Louis, Mo.).

Vitamin ingredients which may be included in the media of the present invention include biotin, choline chloride, D-Ca$^{++}$-pantothenate, folic acid, i-inositol, niacinamide, pyridoxine, riboflavin, thiamine and vitamin B$_{12}$. These vitamins may be obtained commercially, for example from Sigma (Saint Louis, Mo.).

Inorganic salt ingredients which may be used in the media of the present invention include a calcium salt (e.g., CaCl$_2$), CuSO$_4$, FeSO$_4$, KCl, a magnesium salt (e.g., MgCl$_2$), a manganese salt (e.g., MnCl$_2$), Sodium acetate, NaCl, NaHCO$_3$, Na$_2$HPO$_4$, Na$_2$SO$_4$ and ions of the trace elements selenium, silicon, molybdenum, vanadium, nickel, tin and zinc. These trace elements may be provided in a variety of forms, preferably in the form of salts such as Na$_2$SeO$_3$, Na$_2$SiO$_3$, (NH$_4$)$_6$Mo$_7$O$_{24}$, NH$_4$VO$_3$, NiSO$_4$, SnCl and ZnSO. These inorganic salts and trace elements may be obtained commercially, for example from Sigma (Saint Louis, Mo.).

The specific combinations of the above ingredients, their concentration ranges and preferred concentrations in the basal media are shown in Table 1.

TABLE 1

ANIMAL EPITHELIAL CELL CULTURE BASAL MEDIUM COMPONENT CONCENTRATIONS.

| Component | Component Ranges (mg/L) about: | A Preferred Embodiment (mg/L) about: | Most Preferred Embodiment (mg/L) about: |
|---|---|---|---|
| Amino Acids | | | |
| L-Alanine | 1–250 | 9 | 9.00 |
| L-Arginine | 10–500 | 425 | 421.40 |
| L-Asparagine | 5–150 | 12 | 12.20 |
| L-Aspartic Acid | 1–100 | 5 | 4.00 |
| L-Cysteine | 2–250 | 42 | 42.00 |
| L-Glutamic Acid | 5–250 | 15 | 14.80 |
| L-Glutamine | 10–2500 | 1025 | 1020.00 |
| Glycine | 1–200 | 8 | 7.60 |
| L-Histidine | 5–250 | 50 | 50.40 |
| L-Isoleucine | 1–100 | 6 | 6.00 |
| L-Leucine | 25–250 | 130 | 131.20 |
| L-Lysine | 10–250 | 55 | 54.90 |
| L-Methionine | 5–200 | 15 | 13.50 |
| L-Phenylalanine | 1–150 | 10 | 10.03 |
| L-Proline | 1–250 | 35 | 34.60 |
| L-Serine | 5–250 | 126 | 126.20 |
| L-Threonine | 5–100 | 25 | 23.80 |
| L-Tryptophan | 2–100 | 10 | 9.30 |
| L-Tyrosine | 5–100 | 12 | 11.68 |
| L-Valine | 5–250 | 70 | 70.20 |
| Other Components | | | |
| Adenine | 1–100 | 24 | 24.00 |
| Ethanolamine | 0.5–5 | 0.6 | 0.60 |
| D-Glucose | 500–5000 | 1500 | 1500.00 |
| HEPES | 1000–5000 | 3350 | 3336.20 |
| Hydrocortisone | 0.01–5 | 0.1 | 0.074 |
| Insulin | 0.5–25 | 5 | 5.00 |
| Lipoic Acid | 0.05–10 | 0.2 | 0.20 |
| Phenol Red | 0.5–15 | 1 | 1.20 |
| Phosphoethanolamine | 0.05–5 | 0.2 | 0.141 |
| Putrescine | 0.01–1 | 0.2 | 0.20 |
| Sodium Pyruvate | 10–200 | 55 | 55.0 |
| Triiodothyronine (T3) | 0.001–1 | 0.01 | 0.0067 |
| Thymidine | 0.05–25 | 0.7 | 0.73 |

TABLE 1-continued

ANIMAL EPITHELIAL CELL CULTURE BASAL MEDIUM COMPONENT CONCENTRATIONS.

| Component | Component Ranges (mg/L) about: | A Preferred Embodiment (mg/L) about: | Most Preferred Embodiment (mg/L) about: |
|---|---|---|---|
| Transferrin | 1–50 | 11 | 11.11 |
| Vitamins | | | |
| Biotin | 0.005–1 | 0.02 | 0.02 |
| Choline Chloride | 1–150 | 14 | 14.00 |
| D-Ca$^{++}$-Pantothenate | 0.05–10 | 0.3 | 0.30 |
| Folic Acid | 0.1–10 | 1 | 0.80 |
| i-Inositol | 1–75 | 18 | 18.00 |
| Niacinamide | 0.01–5 | 0.05 | 0.04 |
| Pyridoxine | 0.005–10 | 0.06 | 0.06 |
| Riboflavin | 0.01–5 | 0.05 | 0.04 |
| Thiamine | 0.05–5 | 0.3 | 0.30 |
| Vitamin B12 | 0.01–5 | 0.5 | 0.50 |
| Inorganic Salts | | | |
| calcium salt (e.g., CaCl$_2$) | 1–25 | 13 | 12.98 |
| CuSO$_4$ | 0.001–0.1 | 0.002 | 0.002 |
| FeSO$_4$ | 0.1–5 | 0.4 | 0.403 |
| KCl | 1–500 | 112 | 112.00 |
| magnesium salt (e.g., MgCl$_2$) | 1–500 | 185 | 182.48 |
| manganese salt (e.g., MnCl$_2$) | 0.000005–0.005 | 0.00002 | 0.00002 |
| Sodium acetate | 50–500 | 300 | 301.00 |
| NaCl | 3000–9000 | 6800 | 6790.0 |
| NaHCO$_3$ | 100–4000 | 160 | 1160.0 |
| Na$_2$HPO$_4$ | 1–500 | 285 | 284.00 |
| Na$_2$SO$_4$ | 0.5–10 | 4 | 3.38 |
| selenium salt (e.g., Na$_2$SeO$_3$) | 0.001–0.1 | 0.005 | 0.00496 |
| silicon salt (e.g., Na$_2$SiO$_3$) | 0.05–0.5 | 0.15 | 0.137 |
| molybdenum salt (e.g., (NH$_4$)$_6$Mo$_7$O$_{24}$) | 0.0001–0.1 | 0.001 | 0.00120 |
| vanadium salt (e.g., NH$_4$VO$_3$) | 0.001–0.01 | 0.0005 | 0.00057 |
| nickel salt (e.g., NiSO$_4$) | 0.0005–0.001 | 0.0001 | 0.00013 |
| tin salt (e.g., SnCl$_2$) | 0.0001–0.001 | 0.0001 | 0.00011 |
| zinc salt (e.g., ZnSO$_4$) | 0.01–5 | 0.15 | 0.133 |

Complete Media

The above ingredients, when admixed together in solution, form a "basal medium" To this basal medium, heparin, epidermal growth factor (EGF), at least one agent increasing intracellular cyclic adenosine monophosphate (cAMP) levels, and at least one fibroblast growth factor (FGF), are added to formulate the complete culture media of the present invention. Heparin, EGF, the cAMP-increasing agent(s) and FGF(s) may be added to freshly formulated basal medium, or they may be admixed as described in detail in Example 1 in a solution of Dulbecco's Phosphate Buffered Saline (DPBS) and stored frozen, preferably at about −20° C. to about −70° C., until being added to basal medium to formulate the complete medium of the present invention. This admixture of heparin, EGF, the cAMP-increasing agent(s) and FGF(s) may be used as a replacement for BPE or other organ/gland extracts in animal cell culture media. The admixture may also be prepared as a 1×–1000×formulation, most preferably as a 1×, 100×, 500× or 1000×formulation, which is then diluted appropriately into culture medium to provide a 1×final formulation in the complete media of the present invention as described in detail in Example 1.

Heparin may be obtained commercially, for example from Sigma (Saint Louis, Mo.), and is preferably derived from porcine mucosa. Heparin is added to the present media primarily to stabilize the activity of the growth factor components, especially FGF (Gospodarowicz, D., and Cheng, J., *J. Cell. Physiol.* 128:475–484 (1986); EP 0 408 146). To formulate the medium of the present invention, heparin is added to the basal medium shown in Table 1 at a concentration of about 1–500 U.S.P. units/liter, preferably about 5–50 U.S.P. units/liter, and most preferably about 10 U.S.P. units/liter.

EGF may be natural or recombinant and may be human or rodent. EGF is available commercially (e.g., from GIBCO/LTI, Gaithersburg, Md.), or may be isolated from natural sources or produced by recombinant DNA techniques (U.S. Pat. No. 4,743,679) according to methodologies that are routine in the art. To formulate the medium of the present invention, EGF should be added to the basal medium shown in Table 1 at a concentration of about 0.00001–10 mg/L, preferably about 0.0001–0.1 mg/L, and most preferably about 0.0002 mg/L.

A variety of agents that increase intracellular cAMP levels may be used in formulating the media of the present invention. Included are agents which induce a direct increase in intracellular cAMP levels (e.g., dibutyryl cAMP), agents which cause an increase in intracellular cAMP levels by an interaction with a cellular G-protein (e.g., cholera toxin and forskolin), agents which cause an increase in intracellular cAMP levels by acting as agonists of β-adrenergic receptors (e.g., isoproterenol) and agents which cause an increase in intracellular cAMP levels by inhibiting the activities of cAMP phosphodiesterases (e.g., isobutylmethylxanthine (IBMX) and theophylline). Most preferable for use in formulating the media of the present invention is isoproterenol. These cAMP-increasing agents are available commercially, e.g. from Sigma (St. Louis, Mo.), and are used at concentrations approximating those described in Green (*Proc. Natl. Acad. Sci. USA* 15:801–811 (1978)). For example, cholera toxin is added to the basal medium described above at a concentration of about 0.000005–1 mg/L, preferably about 0.0007–0.1 mg/L, and most preferably about 0.08 mg/L. Dibutyryl cAMP is added to the basal media at a concentration of about 25–750 mg/L, preferably about 45–500 mg/L, and most preferably about 148 mg/L. IBM may be added to the basal media at a concentration of about 0.2–25 mg/L, preferably about 2–10 mg/L, and most preferably about 7 mg/L. Most preferably, isoproterenol is the agent used to increase intracellular cAMP levels, and is formulated into the basal media at a concentration of about 0.01–10 mg/L, preferably about 0.1–5 mg/L, and most preferably about 0.25 mg/L The FGF used in formulating the media of the present invention may be any member of the FGF family of growth factors, including FGF-1 (acidic FGF or aFGF), FGF-2 (basic FGF or bFGF), FGF-3 (int-2), FGF4 (K-FGF), FGF-5 (hst-1), FGF-6 (hst-2) and FGF-7 (keratinocyte growth factor or KGF). Preferable are aFGF, bFGF and KGF, and most preferable is aFGF. Natural or recombinant FGF may be used, which may be of human, bovine, porcine or rodent origin. Most preferably, recombinant human aFGF is used in formulating the present media. aFGF, bFGF and KGF are available commercially (e.g., from GIBCO/LTI, Gaithersburg, Md. and R&D Systems, Inc., Minneapolis, Minn.), or may be isolated from natural sources or produced by recombinant DNA techniques (EP 0 408 146 and U.S. Pat. No. 5,395,756 for aFGF; U.S. Pat. No. 5,189,148 for bFGF; WO 90/08771 and WO 95/01434 for KGF) according to methodologies that are routine in the art. To formulate the medium of the present invention, FGF should be added to the basal medium shown in Table 1 at a concentration of about 0.0001–10 mg/L, preferably about 0.001–0.1 mg/L, and most preferably about 0.005 mg/L.

Together, the basal medium, heparin, EGF, cAMP-increasing agent(s) and FGF(s) formulate complete culture media according to the present invention. These complete media are suitable for use in the culture of a variety of animal epithelial cells, as described in more detail below. It may be preferable, however, to further enrich the nutritional content of the complete media to support faster growth and enhanced production of biologicals by the cultured cells, and to provide a more suitable environment for the culture of fastidious animal epithelial cells. To accomplish such enrichment, ascorbic acid may be added to the complete media. Ascorbic acid is available commercially in several forms. Preferable for use in formulating the present media is L-ascorbic acid phosphate, magnesium salt, available from Wako Pure Chemical Industries, which is added to the media at a concentration of about 0.001–10 mg/L, preferably about 0.01–5 mg/L, and most preferably about 0.1 mg/L.

The medium ingredients can be dissolved in a liquid carrier or maintained in dry form. If dissolved in a liquid carrier at the preferred concentrations shown in Table 1 (i.e., a "1×formulation"), the pH of the medium should be adjusted to about 7.0–7.6, preferably about 7.1–7.5, and most preferably about 7.2–7.4. The osmolarity of the medium should also be adjusted to about 275–350 mOsm, preferably about 285–325 mOsm, and most preferably about 280–310 mOsm. The type of liquid carrier and the method used to dissolve the ingredients into solution vary and can be determined by one of ordinary skill in the art with no more than routine experimentation. Typically, the medium ingredients can be added in any order.

Preferably, the solutions comprising ingredients are more concentrated than the concentration of the same ingredients in a 1×media formulation. The ingredients can be 10-fold more concentrated (10×formulation), 25-fold more concentrated (25×formulation), 50-fold more concentrated (50× concentration), or 100-fold more concentrated (100× formulation). More highly concentrated formulations can be made, provided that the ingredients remain soluble and stable. See U.S. Pat. No. 5,474,931, which is directed to methods of solubilizing culture media components at high concentrations.

If the media ingredients are prepared as separate concentrated solutions, an appropriate (sufficient) amount of each concentrate is combined with a diluent to produce a 1×medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.1–1.0 μm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1×sterile medium formulation. Autoclaving or other elevated temperature-based methods of sterilization are not favored, since many of the components of the present culture media are heat labile and will be irreversibly degraded by temperatures such as those achieved during most heat sterilization methods.

The optimal concentration ranges for the basal medium ingredients are listed in Table 1. These ingredients can be combined to form the basal animal cell culture medium which is then supplemented as described above with heparin, EGF, at least one agent increasing intracellular cAMP levels, at least one FGF and optionally with ascorbic acid, to formulate the complete media of the present invention. As will be readily apparent to one of ordinary skill in the art, the concentration of a given ingredient can be increased or decreased beyond the range disclosed and the effect of the increased or decreased concentration can be determined using only routine experimentation. In a preferred embodiment, the concentrations of the ingredients of the medium of the present invention are the concentrations listed in the far right column of Table 1, supplemented with heparin, EGF, aFGF, isoproterenol and ascorbic acid as described above.

As will be readily apparent to one of ordinary skill in the art, each of the components of the culture medium may react with one or more other components in the solution. Thus, the present invention encompasses the formulations disclosed in Table 1, supplemented as described above, as well as any reaction mixture which forms after these ingredients are combined.

The optimization of the present media formulations was carried out using approaches described by Ham (Ham, R. G., *Methods for Preparation of Media, Supplements and Substrata for Serum-Free Animal Culture*, Alan R. Liss, Inc., New York, pp. 3–21 (1984)) and Waymouth (Waymouth, C., *Methods for Preparation of Media, Supplements and Substrata for Serum-Free Animal Culture*, Alan R. Liss, Inc., New York, pp. 23–68 (1984)). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth or continued health of the animal cells is measured.

Use of Culture Media

Cells which can be grown in the medium of the present invention are those of animal origin, including but not limited to cells obtained from mammals. Mammalian cells particularly suitable for cultivation in the present media include epithelial cells of human origin, which may be primary cells derived from a tissue sample such as keratinocytes, cervical epithelial cells, bronchial epithelial cells or tracheal epithelial cells, or transformed cells or established cell lines (e.g., the HCAT human keratinocyte or HeLa cervical epithelial cell lines). These cells may be normal cells, or may optionally be diseased or genetically altered. Other mammalian cells, such as CHO cells, COS cells, VERO cells, BHK cells (including BHK-21 cells) and derivatives thereof, are also suitable for cultivation in the present media. Particularly preferred are primary or secondary human keratinocytes derived from a sample of normal or abnormal human skin. Epithelial tissues, organs and organ systems derived from animals or constructed in vitro or in vivo using methods routine in the art may similarly be cultivated in the culture media of the present invention.

Isolation of Cells

Animal cells for culturing by the present invention may be obtained commercially, for example from ATCC (Rockville, Md.), Cell Systems, Inc. (Kirkland, Wash.), Clonetics Corporation (San Diego, Calif.), BioWhittaker (Walkersville, Md.), or Cascade Biologicals (Portland, Oreg.). Alternatively, cells may be isolated directly from samples of animal tissue obtained via biopsy, autopsy, donation or other surgical or medical procedure.

Tissue should be handled using standard sterile technique and a laminar flow safety cabinet. In the use and processing of all human tissue, the recommendations of the U.S. Department of Health and Human Services/Centers for Disease Control and Prevention should be followed (*Biosafety in Microbiological and Biomedical Laboratories*, Richmond, J. Y. et al., Eds., U.S. Government Printing Office, Washington, D.C. 3rd Edition (1993)). The tissue should be cut into small pieces (e.g., 0.5×0.5 cm) using sterile surgical instruments. The small pieces should be washed twice with sterile saline solution supplemented with antibiotics as above, and then may be optionally treated with an enzymatic solution (e.g., collagenase or trypsin solutions, each available commercially, for example, from GIBCO/LTI, Gaithersburg, Md.) to promote dissociation of cells from the tissue matrix.

The mixture of dissociated cells and matrix molecules are washed twice with a suitable physiological saline or tissue culture medium (e.g., Dulbecco's Phosphate Buffered Saline without calcium and magnesium). Between washes, the cells are centrifuged (e.g., at 200×g) and then resuspended in serum-free tissue culture medium. Aliquots are counted using an electronic cell counter (such as a Coulter Counter). Alternatively, the cells can be counted manually using a hemocytometer.

Plating of Cells

The isolated cells can be plated according to the experimental conditions determined by the investigator. The examples below demonstrate at least one functional set of culture conditions useful for cultivation of certain mammalian cells. It is to be understood, however, that the optimal plating and culture conditions for a given animal cell type can be determined by one of ordinary skill in the art using only routine experimentation. For routine culture conditions, using the present invention, cells can be plated onto the surface of culture vessels without attachment factors. Alternatively, the vessels can be precoated with natural, recombinant or synthetic attachment factors or peptide fragments (e.g., collagen or fibronectin, or natural or synthetic fragments thereof). Isolated cells can also be seeded into or onto a natural or synthetic three-dimensional support matrix such as a preformed collagen gel or a synthetic biopolymeric material. Use of attachment factors or a support matrix with the medium of the present invention will enhance cultivation of many attachment-dependent cells in the absence of serum supplementation.

The cell seeding densities for each experimental condition can be optimized for the specific culture conditions being used. For routine culture in plastic culture vessels, an initial seeding density of 1–5×10$^6$ cells per cm$^2$ is preferable.

Mammalian cells are typically cultivated in a cell incubator at about 37° C. The incubator atmosphere should be humidified and should contain about 3–10% carbon dioxide in air, although cultivation of certain cell lines may require as much as 20% carbon dioxide in air for optimal results. Culture medium pH should be in the range of about 7.1–7.6, preferably about 7.1–7.4, and most preferably about 7.1–7.3.

Cells in closed or batch culture should undergo complete medium exchange (i.e., replacing spent media with fresh media) about every 1–2 days, or more or less frequently as required by the specific cell type. Cells in perfusion culture (e.g., in bioreactors or fermenters) will receive fresh media on a continuously recirculating basis.

Cell Culture Compositions

The cell culture media of the present invention may also be used to produce cell culture compositions comprising the present media and an animal epithelial cell. Animal epithelial cells which may be used to formulate the cell culture compositions of the present invention are those of animal origin, including but not limited to cells obtained from mammals. Mammalian cells particularly suitable for use in formulating the present cell culture compositions include epithelial cells of human origin, which may be primary cells derived from a tissue sample such as keratinocytes, cervical epithelial cells, bronchial epithelial cells or tracheal epithelial cells, or transformed cells or established cell lines (e.g., the HCAT human keratinocyte or HeLa cervical epithelial cell lines), or derivatives thereof. These cells may be normal cells, or may optionally be diseased or genetically altered. Other mammalian cells, such as CHO cells, COS cells, VERO cells, BHK cells (including BHK-21 cells) and derivatives thereof, are also suitable for use in formulating the present cell culture compositions. Particularly preferred are primary or secondary human keratinocytes derived from a sample of normal or abnormal human skin. Epithelial tissues, organs and organ systems derived from animals or constructed in vitro or in vivo using methods routine in the art may similarly be used to formulate the cell culture compositions of the present invention. These cell culture compositions may be used in a variety of medical (including diagnostic and therapeutic), industrial, forensic and research applications requiring ready-to-use cultures of animal epithelial cells in serum-free media.

Having now described the present invention in detail, the same will be more clearly understood by reference to the following examples, which are included herewith for purposes of illustration only and are not intended to be limiting of the invention.

EXAMPLES

Materials and Methods

In each of the following examples, the following materials and methods were generally used.

Isolation and Culture of Human Keratinocytes

Unless otherwise indicated, all media and reagents were obtained from GIBCO/LTI (Gaithersburg, Md.). Human neonatal foreskins were placed in serum-free medium (SFM) without growth factors containing 5 µg/ml gentamycin and were stored at 4° C. Foreskins can be stored in this manner for about five days without significant loss of cell viability. Foreskins were briefly rinsed in 70% isopropanol and then placed into Dulbecco's phosphate-buffered saline (DPBS), without $Ca^{++}$ and $Mg^{++}$, containing 20 µg/ml gentamycin for 60 minutes. Foreskins were then cut into halves or quarters, depending upon the size of the tissue, and the pieces were transferred, dermis side down, to a petri dish containing 25 units/ml dispase, and were incubated 18–24 hours at 4° C. Epidermal sheets were separated from the full-thickness skin with forceps, pooled in 60 mm culture dishes containing 5–7 ml of 0.05% trypsin/0.53 mM EDTA, and were incubated at 37° C. for 15–20 minutes with gentle pipetting to aid in tissue dissociation. Pooling of the tissue specimens is performed to reduce the effects of donor-to-donor growth variation. Trypsin activity was terminated by addition of soybean trypsin inhibitor (10 mg/ml in DPBS). Any remaining pieces of epidermal sheets were carefully removed and discarded. The cell suspension was transferred to a sterile centrifuge tube and the cells pelleted by centrifugation at 40×g for 5 minutes at 22° C., and washed once with SFM. The supernatant was discarded, the cell pellet resuspended in the appropriate medium, and cell densities determined using a hemacytometer. Cells were plated in culture flasks or dishes.

Secondary cultures were established by removing the spent medium, briefly washing the cell monolayer with Versene (1:5000 dilution), and adding an appropriate volume of 0.05% trypsin/0.53 mM EDTA. Cells were incubated at 37° C. until they became round (about 5 minutes), trypsin was removed, and the cells were incubated at 37° C. until they detached from the culture surface with gentle tapping (about 5 minutes). Trypsin activity was inactivated by addition of 10 mg/ml soybean trypsin inhibitor solution; cells were pelleted by centrifugation at 40×g for 5 minutes at 22° C., washed once with SFM, and resuspended in the appropriate medium. Secondary cell cultures were also established from primary keratinocytes obtained from Cell Systems Corporation (Kirkland, Wash.) with results comparable to those found with cultures established from neonatal foreskins.

Trypsinization times are critical to the performance of any keratinocyte medium. Human keratinocytes that remain in trypsin too long have lower plating efficiencies and may be induced to differentiate.

Cultures were incubated at 37° C. in a humidified atmosphere consisting of 5% $CO_2$/95% air. Stock cultures were maintained at a split ratio of 1:2 to 1:3 and subcultured at 70% to 80% confluence. Keratinocytes at passage 0 through passage 4 were used for experimental evaluation.

Morphology and Growth Assays

Morphological analysis and immunostaining of cells were performed in 8-chamber glass culture slides. Keratinocytes were plated at $2 \times 10^4$ cells/$cm^2$ in a total volume of 400 µl/0.8 $cm^2$ chamber. Cells were incubated for 24 hours, then fixed with 3.7% formaldehyde, permeabilized with 0.5% TRITON X-100 in DPBS, and allowed to react with rabbit anti-cytokeratin 14 antibody (1:200 dilution). Cells labeled with antibodies were visualized using goat anti-rabbit F(ab')$_2$ FITC conjugate (1:50 dilution).

Human keratinocyte growth assays were performed in 24-well culture dishes (2 cm2 growth area) utilizing a seeding density of $1 \times 10^4$ cells/$cm^2$. Endpoint growth assays were assessed at 6 days postseeding for primary cells and 72 hours for secondary cells. Growth kinetic assays were counted at 24 hour intervals over 96 hours without medium replacement. Single-cell cloning assays were performed in 96-well tissue culture-treated plates by serial dilution of cell suspensions to 5 cells/ml in the appropriate medium and plating 100 µl/well. Plates were incubated for 5 days before observation. In comparison assays, media of the present invention were examined for their growth-promoting abilities relative to a defined human keratinocyte medium derived from Supplier A and to a BPE-containing formulation (Keratinocyte-SFM; GIBCO/LTI, Gaithersburg, Md.).

Example 1

Formulation of Complete Medium

Formulation of Basal Cell Culture Medium. Distilled, deionized water (hereinafter "dd$H_2O$") was measured out to 80% of the total desired volume. While gently stirring this water with a magnetic stirrer, the following were added: L-alanine (9.00 mg/L), L-arginine.HCl (421.40 mg/L), L-asparagine.HCl (12.20 mg/L), L-aspartic acid (4.00 mg/L), L-cysteine.HCl.H$_2$O (42.00 mg/L), L-glutamic acid (14.80 mg/L), L-glutamine (1020.00 mg/L), glycine (7.60 mg/L), L-histidine.HCl.H$_2$O (50.40 mg/L), L-isoleucine (6.00 mg/L), L-leucine (131.20 mg/L), L-lysine.HCl (54.90 mg/L), L-methionine (13.50 mg/L), L-phenylalanine (10.03 mg/L), L-proline (34.60 mg/L), L-serine (126.20 mg/L), L-threonine (23.80 mg/L), L-tryptophan (9.30 mg/L), L-tyrosine-disodium salt (11.68 mg/L), L-valine (70.20 mg/L), biotin (0.02 mg/L), D-Ca$^{++}$-pantothenate (0.30 mg/L), choline chloride (14.00 mg/L), folic acid (0.8 mg/L), i-inositol (18.00 mg/L), niacinamide (0.04 mg/L), pyridoxine.HCl (0.06 mg/L), riboflavin (0.04 mg/L), thiamine-HCl (0.30 mg/L), vitamin B12 (0.50 mg/L), putrescine.2HCl (0.20 mg/L), D-glucose (1500.0 mg/L), KCl (112.0 mg/L), NaCl (6790.0 mg/L), thymidine (0.73 mg/L), adenine (24.00 mg/L), HEPES (3336.20 mg/L), lipoic acid (0.20 mg/L), phenol red (1.20 mg/L), sodium pyruvate (55.0 g), sodium acetate (301.00 mg/L), Na$_2$HPO$_4$ (284.00 mg/L), Na$_2$SO$_4$ (3.39 mg/L), human insulin (5.00 mg/L) and human transferrin (11.11 mg/L).

A stock solution of ethanolamine.HCl was prepared in ddH$_2$O at 976.00 mg/L/L and 0.615 ml/L of this stock was added to the medium solution, to give a final concentration of ethanolamine.HCl of 0.60 mg/L.

A stock solution of phosphoethanolamine was prepared in ddH2O at 1408.00 mg/L and 0.1001 ml/L of this stock was added to the medium solution, to give a final concentration of phosphoethanolamine of 0.141 mg/L.

A stock solution of FeSO$_4$.7H$_2$O (41.70 mg/L), MgCl$_2$.6H$_2$O (18890 mg/L), and CaCl$_2$.2H$_2$O (1344 mg/L) was prepared in water containing 0.5 ml/L concentrated HCl, and 9.660 ml of this stock solution was added to the medium solution, to give final concentrations of 0.403 mg/L FeSO$_4$.7H$_2$O, 182.48 mg/L MgCl$_2$.6H$_2$O and 12.98 mg/L CaCl$_2$.2H$_2$O.

A stock solution of ZnSO$_4$.7H$_2$O (137.68 mg/L) was prepared in water, and 0.9660 ml of this solution was added to the medium solution to give a final concentration of 0.133 mg/L ZnSO$_4$.7H$_2$O.

A stock solution containing Na$_2$SeO$_3$ (0.513 mg/L), (NH$_4$)$_6$Mo$_7$O$_{24}$.4H$_2$O (0.124 mg/L), NaSiO$_3$.9H$_2$O (14.2 mg/L), NiSO$_4$.6H$_2$O (0.013 mg/L), MnCl$_2$.4H$_2$O (0.002 mg/L), SnCl$_2$.2H$_2$(0.011 mg/L) and NH$_4$VO$_3$ (0.059 mg/L) was prepared in water with 0.5 ml/L concentrated HCl, and 9.660 ml of this stock solution was added to the medium solution to give final concentrations of 0.00496 mg/L Na$_2$SeO$_3$, 0.00120 mg/L (NH$_4$)$_6$Mo$_7$O$_{24}$.4H$_2$O, 0.137 mg/L NaSiO$_3$.9H$_2$O, 0.00013 mg/L NiSO$_4$.6H$_2$O, 0.00002 mg/L MnCl$_2$.4H$_2$O, 0.00011 mg/L SnCl$_2$.2H$_2$O and 0.00057 mg/L NH$_4$VO$_3$.

A stock solution of hydrocortisone was prepared at 370 mg/L in 95% ethanol, and 0.2 ml of this stock was added to the medium solution to give a final concentration of hydrocortisone of 0.074 mg/L.

A stock solution of triiodothyronine (T3) was prepared at 67.00 mg/L in 70% ethanol, and 0.1 ml of this stock was added to the medium solution to give a final concentration of T3 of 0.0067 mg/L.

NaHCO$_3$ (1160 mg/L) was added to the medium solution, and the pH of the solution was then adjusted with HCl to 7.2±0.05 and the volume adjusted to the full desired volume with ddH$_2$O. The osmolality was determined to be 290±15 mOsm.

This basal medium formulation was then filtered through a low protein-binding filter, bottled and stored under diminished light conditions at 4° C. until use.

Formulation of the Growth Supplement. To a solution of Dulbecco's Phosphate Buffered Saline (DPBS) the following were added while gently stirring: ascorbic acid phosphate, magnesium salt (50 mg/L), aFGF (2.5 mg/L), heparin (5000 units/L) and EGF (0.1 mg/L).

A stock solution of isoproterenol (100,000 mg/L) was prepared in DPBS containing 50 mg/L ascorbic acid, and 1.25 ml/L of this solution was added to the above, to form a 500×formulation of the growth supplement.

This 500×solution was then filtered through a low protein-binding filter, and added to the basal medium or aliquotted and stored at −20 to −80° C. until use in epithelial cell culture medium as a replacement for an organ or gland extract such as BPE.

Preparation of the Complete Medium. One ml of the growth supplement was added to 500 ml of the basal medium, and the complete medium was used immediately or stored at 4° C. under diminished light conditions until use.

Example 2

Effects of aFGF

To examine the utility of the basal medium in supporting the growth of human keratinocytes, and to determine the effects of FGF, primary human keratinocytes were isolated as described above and cultured in the basal medium from Example 1 supplemented with 10 U.S.P. units/L heparin and 0.0002 mg/L EGF, or in the basal medium containing 10 U.S.P. units/L heparin, 0.0002 mg/L EGF and 0.005 mg/L aFGF. Representative results of five separate experiments, comparing growth in the basal medium with and without aFGF to that in a BPE-containing keratinocyte SFM ("control") are shown in Table 2.

TABLE 2

EFFECTS OF aFGF (CELLS/ML × 10$^5$).

| Control | Defined SFM (Present Invention) | |
|---|---|---|
| | − aFGF | + aFGF |
| 1.85 | 0.738 | 0.860 |
| 1.86 | 0.924 | 0.970 |
| 0.844 | 0.686 | 0.756 |
| 4.38 | 3.40 | 3.54 |
| 3.66 | 3.76 | 4.00 |

These results indicate that the basal medium supports the growth of primary keratinocytes, albeit usually to a lesser extent than BPE-containing control medium. Furthermore, the results indicate that the addition of aFGF to the basal medium enhances its ability to promote the growth of keratinocytes.

Example 3

Effects of Isoproterenol

To determine if the performance of the defined culture medium could be further enhanced by inclusion of an agent that raises intracellular cAMP levels, the basal medium containing heparin, EGF and aFGF from Example 2 was examined with and without the addition of 0.25 mg/L isoproterenol. Primary human keratinocytes were isolated and cultured as described for Example 2. Representative results of five separate experiments, comparing growth in the medium with and without isoproterenol to that in a BPE-containing keratinocyte SFM ("control") are shown in Table 3.

TABLE 3

EFFECTS OF ISOPROTERENOL
(CELLS/ML × $10^5$).

| Control | Defined SFM (Present Invention) | |
|---|---|---|
| | − isoproterenol | + isoproterenol |
| 0.604 | 0.564 | 0.765 |
| 1.234 | 0.922 | 1.443 |
| 0.819 | 0.565 | 1.177 |
| 1.396 | 0.956 | 1.777 |
| 1.772 | 0.674 | 1.776 |

These results demonstrate that the addition of isoproterenol to the aFGF-containing basal medium of the present invention further enhances its ability to promote the growth of keratinocytes. In fact, the medium containing aFGF and isoproterenol promoted the growth of primary human keratinocytes better than did the BPE-containing control. These findings thus indicate that a defined medium comprising the basal medium, hepari, EGF, aFGF and isoproterenol is an optimal formulation for a fully defined, BPE-free SFM that supports cultivation and promotes growth of human keratinocytes. Furthermore, these results demonstrate that a composition comprising heparin, EGF, FGF and a cAMP-activating agent such as isoproterenol may be used as a replacement for an organ or gland extract such as BPE in SFM for the culture of epithelial cells such as keratinocytes.

Example 4

Effects of Ascorbic Acid

Since some basal media used in the culture of keratinocytes contain ascorbic acid (Gilchrest, B. A., et al., *J. Cell. Physiol.* 120:377–383 (1984)), the effect of the addition of 50.0 mg/L ascorbic acid to the EGF/aFGF/isoproterenol-containing medium from Example 3 was examined. Primary human keratinocytes were isolated and cultured as described for Example 2. Representative results of four separate experiments, comparing growth in the medium with and without ascorbic acid to that in a BPE-containing keratinocyte SFM ("control") are shown in Table 4.

TABLE 4

EFFECTS OF ASCORBIC ACID
(CELLS/ML × $10^5$).

| Control | Defined SFM (Present Invention) | |
|---|---|---|
| | − ascorbic acid | + ascorbic acid |
| 1.107 | 1.088 | 1.221 |
| 6.258 | 11.61 | 14.10 |
| 0.801 | 1.475 | 1.492 |
| 1.860 | 2.290 | 2.860 |

These results demonstrate that the addition of ascorbic acid to the aFGF/isoproterenol-containing medium of the present invention further enhances its ability to promote the growth of keratinocytes. The effects of ascorbic acid, however, were not as dramatic as those observed for the addition of either aFGF (Example 2) or isoproterenol (Example 3); the defined medium containing ascorbic acid performed only marginally better than that without ascorbic acid, suggesting that the inclusion of ascorbic acid in the defined medium of the present invention may be optional. Both defined media, however, significantly outperformed the control medium, confirming the results obtained in Example 3.

Together, the findings of Examples 2–4 indicate that a defined medium comprising the basal medium, heparin, EGF, aFGF and isoproterenol, and optionally including ascorbic acid, is an optimal formulation for a fully defined, BPE-free SFM that supports cultivation and promotes growth of human keratinocytes. In addition, these results demonstrate that a solution comprising heparin, EGF, FGF, a cAMP-increasing agent such as isoproterenol and ascorbic acid may be used as a replacement for an organ or gland extract such as BPE in SFM for the culture of epithelial cells such as keratinocytes.

Example 5

Growth of Primary Human Keratinocytes in Defined SFM

Primary human keratinocytes were isolated as described above and were cultured in either the defined SFM of the present invention containing EGF, aFGF, isoproterenol and ascorbic acid as described in Example 4 ("Defined Keratinocyte-SFM"), or in a BPE-containing keratinocyte SFM ("Keratinocyte-SFM"). After multiple passages, cultures were isolated, plated and cultured for 24 hours, and cells were then examined by phase contrast microscopy for morphology (FIG. 1) or were stained with antibodies against keratin 14 and examined by fluorescence microscopy for the expression this standard marker of basal human keratinocytes (FIG. 2).

Figure 1B:
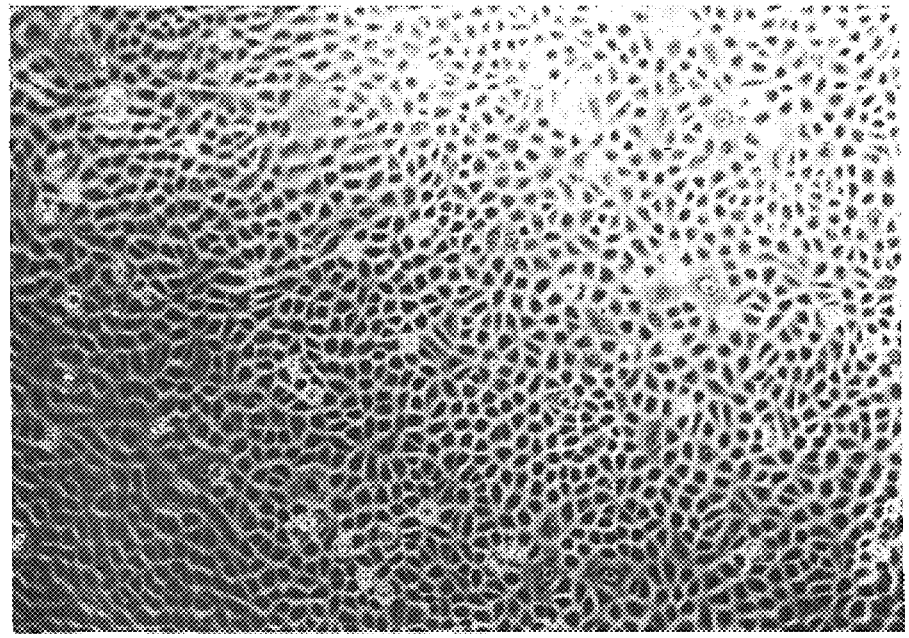
Figure 2:
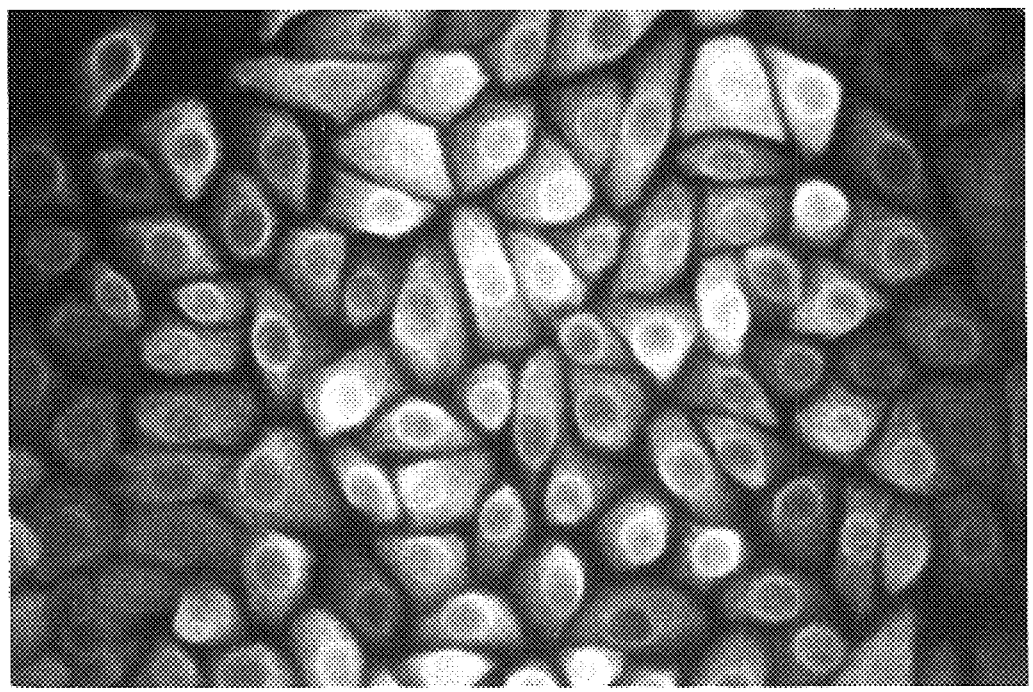
FIG. 2. Photomicrograph of fluorescence microscopy of human keratinocytes cultured in the defined keratinocyte SFM of the present invention and stained with fluorescent antibodies directed against keratin 14.

As shown in FIG. 1, human keratinocytes cultured in the defined medium of the present invention (FIG. 1A) exhibited the same contact-inhibited, "crazy paving" pattern morphology, typical of cultured primary keratinocytes (Daniels, J. T., et al., *Exp. Dermatol.* 4:183 (1995)), observed for cells cultured in the BPE-containing media (FIG. 1B). Monolayer cultures in both media had distinct borders and prominent nuclei, indicating the cultures were in general good health. As demonstrated in FIG. 2, the cells in the defined keratinocyte medium of the present invention stained positively for keratin 14, indicating that the medium of the present invention allows the retention of keratinocyte-specific markers by cultured primary cells. Similar results were obtained with cells cultured in BPE-containing medium.

Figure 3:
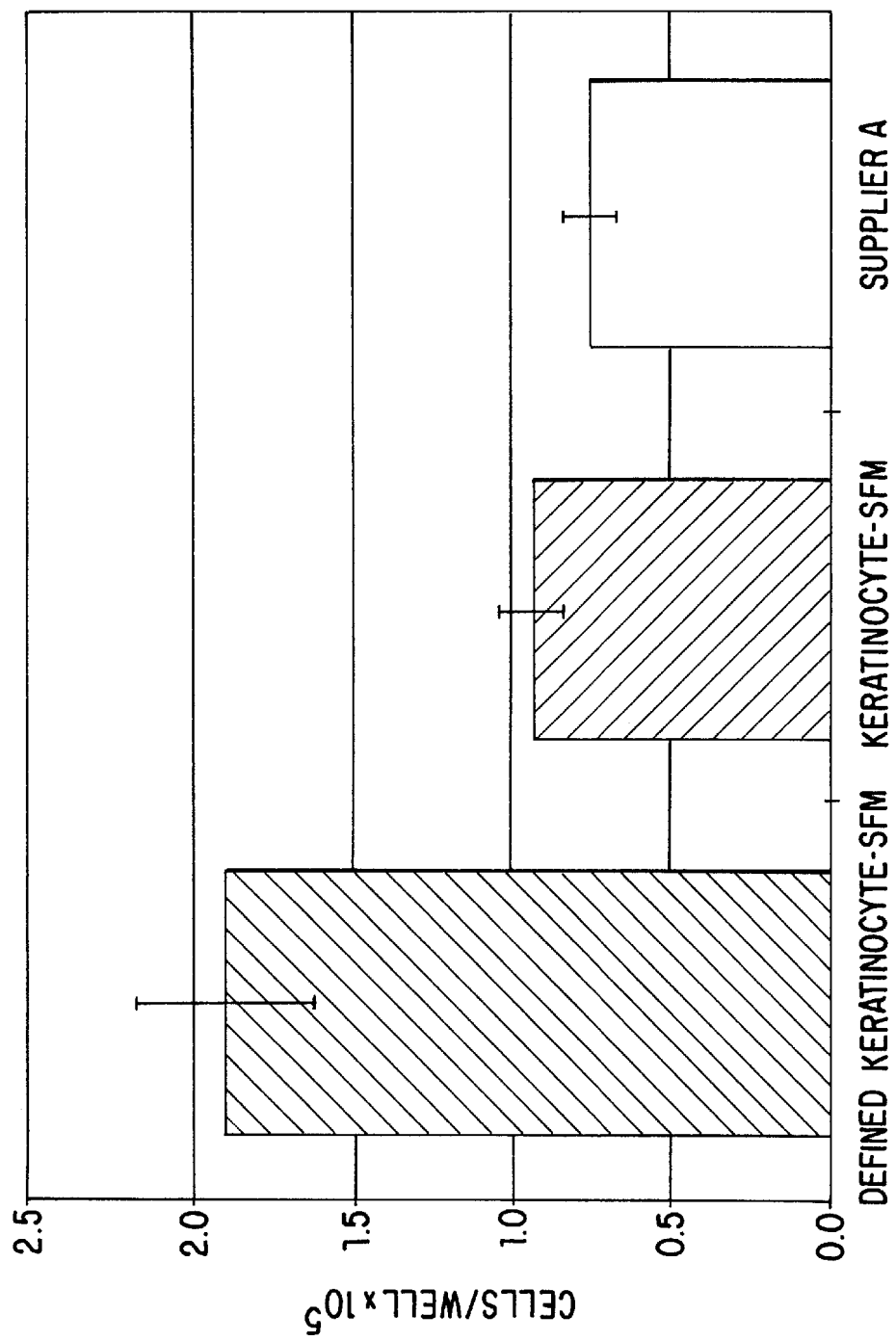
FIG. 3. Bar graph demonstrating growth of primary human keratinocytes in the defined keratinocyte SFM of the present invention ("Defined Keratinocyte-SFM"), in a BPE-containig keratinocyte SFM ("Keratinocyte-SFM") or in a keratinocyte SFM obtained from Hyclone Laboratories (Logan, Utah) ("Supplier A"). Growth was determined six days after seeding, and values represent means±SEM, n=7.

To examine the utility of the media in supporting growth of primary keratinocytes, cells were incubated over 6 days in the medium of the present invention ("Defined Keratinocyte-SFM"), in a BPE-containing keratinocyte SFM ("Keratinocyte-SFM"), or in a defined keratinocyte medium obtained from Hyclone Laboratories ("Supplier A"). As shown in FIG. 3, primary human keratinocytes cultured in the medium of the present invention demonstrated significantly enhanced growth ($p \leq 0.05$) when compared to the other keratinocyte media Population doubling times for each medium were: Defined Keratinocyte-SFM: 46.3±5.9 hours; Keratinocyte-SFM: 66.6±12.8 hours; and Supplier A: 83.5±19.1 hours.

Together, these results indicate that the defined serum-free medium of the present invention supports the growth of primary human keratinocytes, and outperforms even undefined, traditionally used BPE-containing media.

Example 6

Growth of Secondary Human Keratinocytes in Defined SFM

Figure 4:
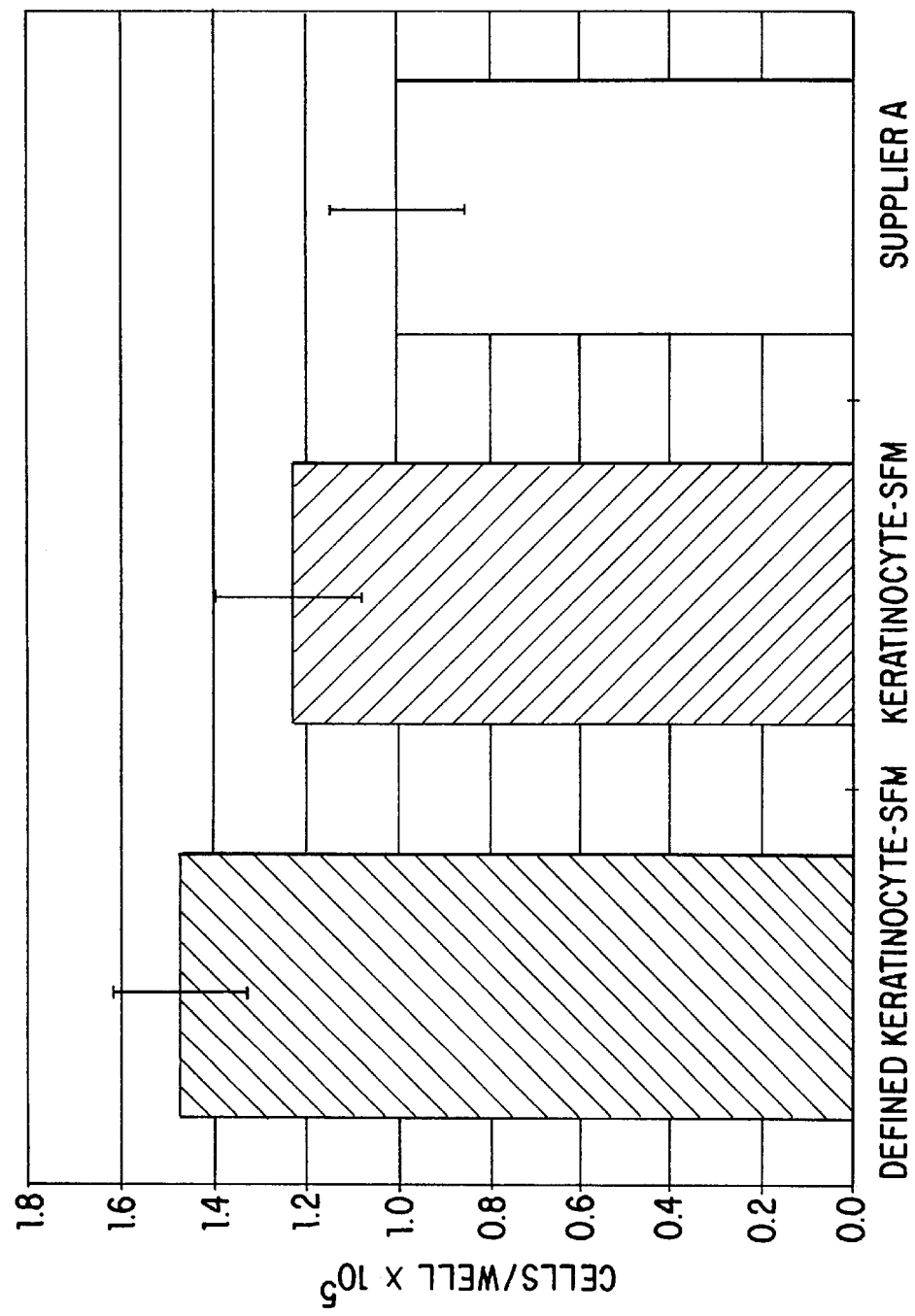
FIG. 4. Bar graph demonstrating growth of secondary human keratinocytes in the defined keratinocyte SFM of the present invention ("Defined Keratinocyte-SFM"), in a BPE-containing keratinocyte SFM ("Keratinocyte-SFM") or in a keratinocyte SFM from Hyclone Laboratories ("Supplier A"). Growth was determined 72 hours after seeding, and values represent means±SEM, n=7.

To determine if the utility of the media of the present invention extended to secondary cultures of keratinocytes, cells derived from actively growing cultures or from isolates obtained commercially were cultured in the three media described in Example 5 and examined for growth rate. As demonstrated in FIG. 4, the growth of secondary cultures was similar in the medium of the present invention and in the BPE-containing medium. However, significantly better cell growth ($p<0.05$) was obtained in the present medium than in the defined medium from Supplier A. Population doubling times for these secondary keratinocytes were: Defined Keratinocyte-SFM: 25.0±1.1 hours; Keratinocyte-SFM: 29.0±1.6 hours; and Supplier A: 35.4±4.1 hours.

Figure 5:
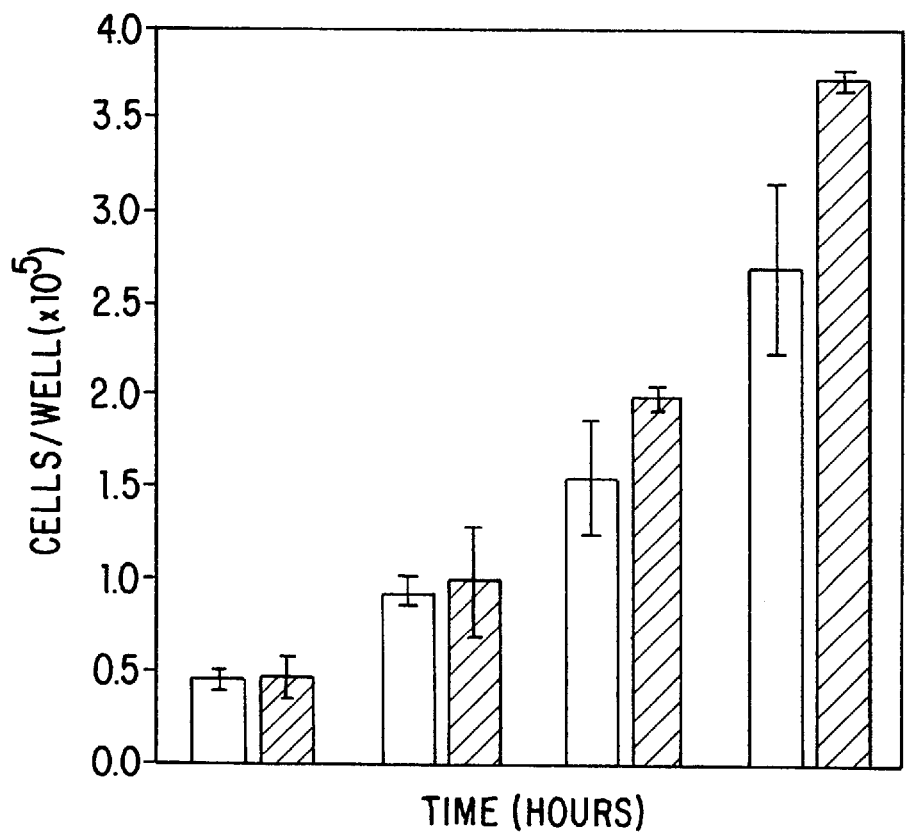
FIG. 5. Bar graph demonstrating growth kinetic analysis of human keratinocytes. Cells were cultured in the defined keratinocyte SFM of the present invention (■) or in a BPE-containing keratinocyte SFM (□). Values represent the mean±SD, n=2.

Daily growth kinetic experiments using secondary cultures of keratinocytes confirmed that cells cultured in the medium of the present invention proliferated at a rate comparable to that of BPE-containing media (FIG. 5). Furthermore, cloning efficiencies of about 40% have been achieved with human keratinocytes cultured in the medium of the present invention in single-cell cloning experiments, comparable to those achieved with cells grown in BPE-containing media (data not shown). In the media of the present invention, secondary cultures can be maintained for at least six passages with split ratios of about 1:2 performed twice weekly.

Taken with those in Example 5, these results indicate that the defined serum-free medium of the present invention supports the growth of primary and secondary human keratinocytes, and outperforms both undefined BPE-containing media and at least one other defined media currently available commercially.

Example 7

Stability of Defined SFM

To evaluate the shelf life of the medium of the present invention, primary human keratinocytes were cultivated for six days in the present media (Defined Keratinocyte-SFM or in BPE-containing media (Keratinocyte-SFM). Media were evaluated weekly over a storage period of 15-weeks after formulation, and cell counts were compared at each time point to those obtained for freshly prepared media.

Figure 6:
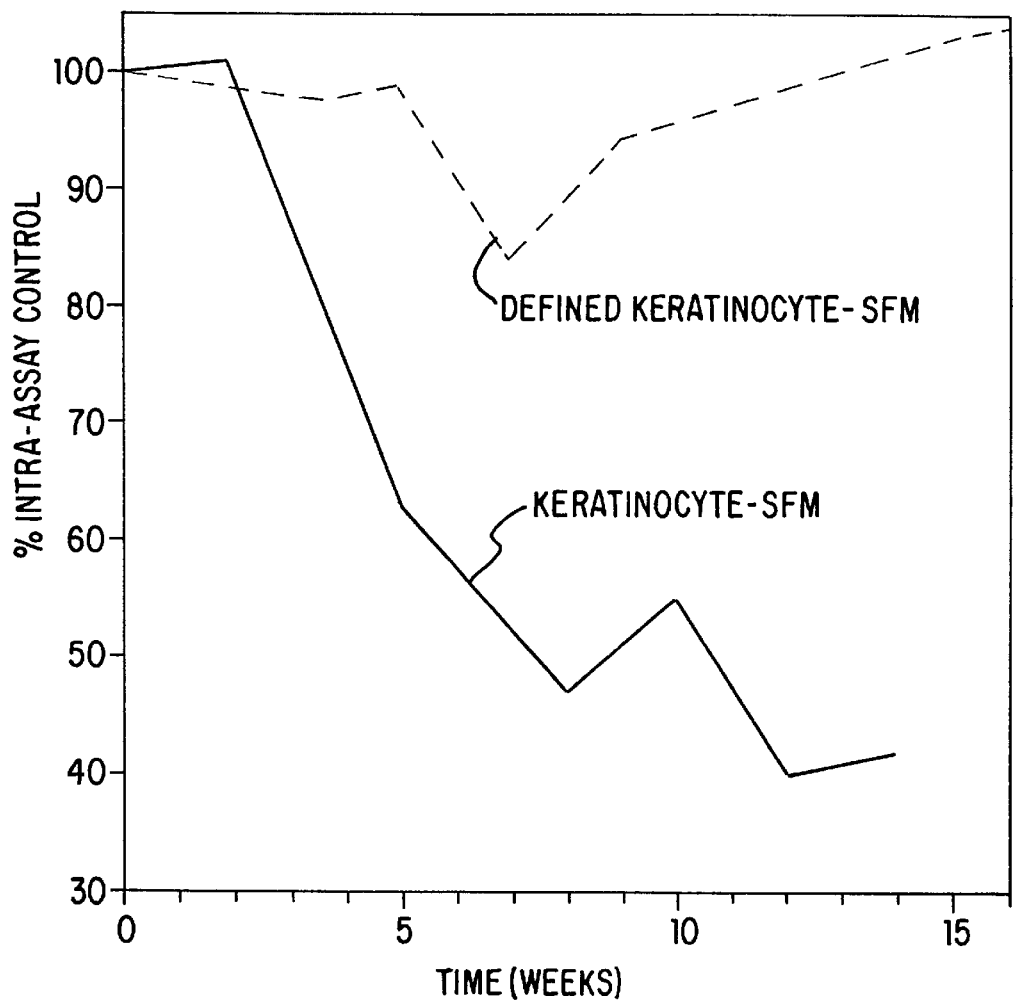
FIG. 6. Line graph demonstrating an evaluation of media shelf life using primary human keratinocytes. Cells were cultured in the defined keratinocyte SFM of the present invention (solid line) or in a BPE-containing keratinocyte SFM (dashed line) over a 15-week period. Cells were counted after 6 days in medium stored for given times and compared to control cells cultured in fresh medium.

As shown in FIG. 6, the fully supplemented defined SFM of the present invention had a shelf life of over 14 weeks, which was considerably longer than the BPE-containing medium. These results indicate that the medium of the present invention, when stored properly as described above, demonstrates an extended shelf life compared to more traditionally used BPE-containing media.

General Discussion

Culture systems designed to propagate human keratinocytes have evolved to reduce the undefined components and to increase culture longevity and cell yields. The results of the above Examples demonstrate that BPE can be replaced in SFM by a solution comprising heparin, EGF, at least one FGF, at least one agent that increases intracellular cAMP levels, and that optionally comprises ascorbic acid. Furthermore, this replacement of BPE may be effected without adversely affecting cellular proliferation rates and the general physiology of human keratinocytes. The removal of BPE as a medium component while maintaining medium performance represents a step forward in human keratinocyte culture by providing a more standardized and controlled culture environment, as has also been shown lacking for other highly used primary cell cultures (Watson, C. A., et al., *Science* 268:447–448 (1995)).

Thus, taken in combination, the results in Examples 1–6 indicate that an optimal culture medium formulation for supporting the cultivation of animal cells is the basal medium formulation shown in Table 1, supplemented with EGF at about 5–10 mg/Liter, aFGF at about 5 mg/Liter, isoproterenol at about 0.3 mg/Liter and ascorbic acid at about 50 mg/Liter (although ascorbic acid may be eliminated with only a slight diminution of growth promotion).

Having now fully described the present invention it will be understood by those of ordinary skill in the art that the same can be performed within a wide and equivalent range of conditions, formulations and other parameters without affecting the scope of the invention or any embodiment thereof.

All publications, patents and patent applications cited herein are indicative of the level of skill of those skilled in the art to which this invention pertains, and are herein incorporated by reference in their entirety.

What is claimed is:

1. A serum-free cell culture medium comprising heparin, epidermal growth factor (EGF), a fibroblast growth factor (FGF) and an agent causing an increase in intracellular levels of cyclic adenosine monophosphate (cAMP), wherein said medium is capable of supporting the cultivation of an animal epithelial cell in vitro.

2. The medium of claim 1, wherein said FGF is selected from the group consisting of FGF-1 (aFGF), FGF-2 (bFGF) and FGF-7 (KGF).

3. The medium of claim 2, wherein said FGF is aFGF.

4. The medium of claim 1, wherein said agent causing an increase in intracellular levels of cAMP functions by directly increasing intracellular cAMP levels.

5. The medium of claim 1, wherein said agent causing an increase in intracellular levels of cAMP functions by inhibiting a cAMP phosphodiesterase.

6. The medium of claim 1, wherein said agent causing an increase in intracellular levels of cAMP is a β-adrenergic receptor agonist.

7. The medium of claim 1, wherein said agent is dibutyryl cAMP.

8. The medium of claim 1, wherein said agent is isobutylmethylxanthine or theophylline.

9. The medium of claim 1, wherein said agent is isoproterenol.

10. The medium of claim 1, said medium further comprising ascorbic acid.

11. The medium of claim 1, wherein said medium is a 1×medium formulation.

12. The cell culture medium of claim 1, wherein said medium formulation is a 10×concentrated medium formulation.

13. The cell culture medium of claim 1, said medium further comprising one or more ingredients selected from the group of ingredients consisting of an amino acid, a vitamin, an inorganic salt, adenine, ethanolamine, D-glucose, N-[2-hydroxyethyl]-piperazine-N'-[2-ethanesulfonic acid] (HEPES), hydrocortisone, insulin, lipoic acid, phenol red, phosphoethanolamine, putrescine, sodium pyruvate, T3, thymidine and transferrin.

14. The medium of claim 13, medium further comprising ascorbic acid.

15. The cell culture medium of claim 13, wherein said amino acid ingredient comprises one or more amino acids selected from the group consisting of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine.

16. The cell culture medium of claim 13, wherein said vitamin ingredient comprises one or more vitamins selected from the group consisting of biotin, choline chloride, D-Ca$^{++}$-pantothenate, folic acid, i-inositol, niacinamide, pyridoxine, riboflavin, thiamine and vitamin $B_{12}$.

17. The cell culture medium of claim 13, wherein said inorganic salt ingredient comprises one or more inorganic salts selected from the group consisting of a calcium salt, $CuSO_4$, $FeSO_4$, KCl, a magnesium salt, a manganese salt, sodium acetate, NaCl, $NaHCO_3$, $NaHPO_4$, $Na_2SO_4$, a selenium salt, a silicon salt, a molybdenum salt, a vanadium salt, a nickel salt, a tin salt and a zinc salt.

18. The medium of claim 1, wherein said animal epithelial cell is selected from the group of animal epithelial cells consisting of a keratinocyte, a cervical epithelial cell, a bronchial epithelial cell and a tracheal epithelial cell.

19. The cell culture medium of claim 18, wherein said cell is a human cell.

20. The cell culture medium of claim 18, wherein said cell is a normal cell.

21. The cell culture medium of claim 18, wherein said cell is an abnormal cell.

22. The cell culture medium of claim 21, wherein said abnormal cell is a transformed cell, an established cell, or a cell derived from a diseased tissue sample.

23. A kit for the culture of an animal epithelial cell, said kit comprising a carrier means having in close confinement therein one or more container means, wherein a first container means contains the culture medium of claim 1 and a second carrier means contains at least one component selected from the group consisting of heparin, epidermal growth factor (EGF), and ascorbic acid.

24. A composition comprising heparin, EGF, a fibroblast growth factor (FGF), and an agent causing an increase in intracellular levels of cyclic adenosine monophosphate (cAMP), wherein said composition replaces an organ or gland extract in an animal cell culture medium.

25. The composition of claim 24, further comprising ascorbic acid.

26. The composition of claim 24, wherein said FGF is selected from the group consisting of FGF-1 (aFGF), FGF-2 (bFGF) and FGF-7 (KGF).

27. The composition of claim 26, wherein said FGF is aFGF.

28. The composition of claim 24, wherein said agent causing an increase in intracellular levels of cAMP functions through interaction with a cellular G-protein.

29. The composition of claim 24, wherein said agent causing an increase in intracellular levels of cAMP functions by directly increasing intracellular cAMP levels.

30. The composition of claim 24, wherein said agent causing an increase in intracellular levels of cAMP functions by inhibiting a cAMP phosphodiesterase.

31. The composition of claim 24, wherein said agent causing an increase in intracellular levels of cAMP is a β-adrenergic receptor agonist.

32. The composition of claim 28, wherein said agent is cholera toxin or forskolin.

33. The composition of claim 29, wherein said agent is dibutyryl cAMP.

34. The composition of claim 30, wherein said agent is isobutylmethylxanthine or theophylline.

35. The composition of claim 31, wherein said agent is isoproterenol.

36. The composition of claim 24, wherein said composition is a 1×–1000×concentrated formulation.

37. The composition of claim 24, wherein said composition is a 1×concentrated formulation.

38. The composition of claim 24, wherein said composition is a 100×concentrated formulation.

39. The composition of claim 24, wherein said composition is a 500×concentrated formulation.

40. The composition of claim 24, wherein said composition is a 1000×concentrated formulation.

41. The cell culture medium of claim 1, wherein said medium comprises the ingredients adenine, ethanolamine, D-glucose, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, T3, thymidine, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-Ca$^{++}$-pantothenate, folic acid, i-inositol, niacinamide, pyridoxine, riboflavin, thiamine, vitamin $B_{12}$, a calcium salt, $CuSO_4$, $FeSO_4$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, and a zinc salt, and wherein each ingredient is present in an amount which supports the cultivation of an animal epithelial cell in vitro.

42. The medium of claim 1, said medium further comprising heparin and epidermal growth factor (EGF).

43. The medium of claim 42, said medium further comprising ascorbic acid.

44. The cell culture medium of claim 1, wherein said cell culture medium comprises one or more additional ingredients selected from the group consisting of adenine, ethanolamine, D-glucose, N-[2-hydroxyethyl]-piperazine-N'-[2-ethanesulfonic acid] (HEPES), hydrocortisone, insulin, lipoic acid, phenol red, phosphoethanolamine, putrescine, sodium pyruvate, T3, thymidine, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-Ca$^{++}$-pantothenate, folic acid, i-inositol, niacinamide, pyridoxine, riboflavin, thiamine, vitamin $B_{12}$, a calcium salt, $CuSO_4$, $FeSO_4$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt and a zinc salt, and wherein each ingredient is added in an amount which supports the cultivation of an animal epithelial cell in vitro.

45. A cell culture medium obtained by combining the medium obtained according to either claim 1 or claim 44 and ascorbic acid.

46. A method of cultivating an animal epithelial cell comprising the steps of
(a) contacting said cell with the cell culture medium of any one of claims 1, 42, or 44; and (b) cultivating said cell under conditions suitable to support cultivation of said cell.

47. The method of claim 46, wherein said animal epithelial cell is selected from the group of animal epithelial cells consisting of a keratinocyte, a cervical epithelial cell, a bronchial epithelial cell and a tracheal epithelial cell.

48. The method of claim 46, wherein said cell is a human cell.

49. The method of claim 46, wherein said cell is a normal cell.

50. The method of claims 46, wherein said cell is an abnormal cell.

51. The method of claim 50, wherein said abnormal cell is a transformed cell, an established cell, or a cell derived from a diseased tissue sample.

52. A kit for the culture of an animal epithelial cell, said kit comprising a carrier means having in close confinement therein one or more container means, wherein a first container means contains the culture medium of any one of claims 1, 42, or 44.

53. A kit for the culture of an animal epithelial cell, said kit comprising a carrier means having in close confinement therein one or more container means, wherein a first container means contains the culture medium of claim 45.

54. A composition comprising the culture medium of any one of claims 1, 42, or 44 and an animal epithelial cell.

55. The composition of claim 54, wherein said animal epithelial cell is selected from the group of animal epithelial cells consisting of a keratinocyte, a cervical epithelial cell, a bronchial epithelial cell and a tracheal epithelial cell.

56. The composition of claim 54, wherein said cell is a human cell.

57. The composition of claim 54, wherein said cell is a normal cell.

58. The composition of claim 54, wherein said cell is an abnormal cell.

59. The composition of claim 58, wherein said abnormal cell is a transformed cell, an established cell, or a cell derived from a diseased tissue sample.

* * * * *